United States Patent [19]
Gallenkamp et al.

[11] Patent Number: 4,874,860
[45] Date of Patent: Oct. 17, 1989

[54] PROCESS FOR PREPARING 1,3,5-TRIAZINETRIONES

[75] Inventors: Bernd Gallenkamp, Wuppertal; Andreas Günther, Cologne; Karl-Heinrich Mohrmann, Bergisch-Gladbach; Thomas Schmidt, Haan, all of Fed. Rep. of Germany

[73] Assignee: Bayer Aktiengesellschaft, Leverkusen, Fed. Rep. of Germany

[21] Appl. No.: 136,253

[22] Filed: Dec. 18, 1987

Related U.S. Application Data

[63] Continuation of Ser. No. 858,407, May 1, 1986, abandoned.

[30] Foreign Application Priority Data

May 9, 1985 [DE] Fed. Rep. of Germany ....... 3516632

[51] Int. Cl.$^4$ ............................................. C07D 251/34
[52] U.S. Cl. .................................. 544/221; 544/222; 544/193; C07D/251/34
[58] Field of Search ........................ 544/221, 222, 193; 564/418

[56] References Cited

U.S. PATENT DOCUMENTS 4,219,552 8/1980 Haberkorn et al. ................. 544/221
4,568,674 2/1986 Haberkorn et al. ................. 544/221

FOREIGN PATENT DOCUMENTS 2115096 10/1972 Fed. Rep. of Germany ...... 548/336

OTHER PUBLICATIONS

Close, JOACS, vol. 75, No. 15, Aug. 1953 pp. 3615–3618.
CA, vol. 100, 1984, 100:102973v. O'Brien et al. CA vol. 92, 1980, 934:46616d.,.
Chande et al., CA vol. 81, 1974, 81:77878x.
March et al. Adv Org Chem Textbook, McGraw-Hill, NY 1977, pp. 384–386.

*Primary Examiner*—John M. Ford
*Attorney, Agent, or Firm*—Sprung Horn Kramer & Woods

[57] ABSTRACT

The novel process

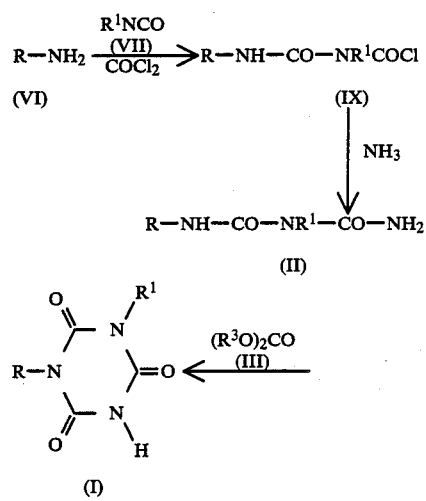

gives the end products, known as animal growth-promoters and coccidiostatics. Intermediates II are new.

2 Claims, No Drawings

PROCESS FOR PREPARING 1,3,5-TRIAZINETRIONES

This is a continuation of application Ser. No. 858,407, filed May 1, 1986, now abandoned.

The invention relates to a new process for preparing 1,3,5-triazinetriones, to intermediates which can be used for carrying out the process, and to a process for preparing such intermediates.

It is already known that 1,3,5-triazinetriones can be prepared from ureas and carbonyl isocyanates.

This method has the disadvantage of using carbonyl isocyanates. The preparation and handling of these compounds on a large scale are fraught with problems. The storage of these intermediates likewise requires extensive safety precautions.

The present invention relates to 1. a process for preparing 1,3,5-triazinetriones of the formula (I)

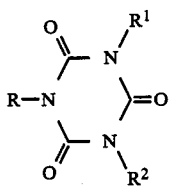

(I)

in which R stands for optionally substituted aryl and $R^1$ and $R^2$ stand for hydrogen, halogen and optionally substituted radicals from the group comprising alkyl, alkoxy, alkylthio, alkylsulphonyl and aryl, which is characterized in that biurets of the formula (II)

R—NH—CO—NR¹—CO—NHR²  (II)

in which R, $R^1$ and $R^2$ have the abovementioned meanings, are reacted with dialkyl carbonates of the formula (III)

(R³O)₂CO  (III)

in which $R^3$ stands for alkyl, in the presence of strong bases and if desired in the presence of diluents;

2. new biurets of the formula (II)

R—NH—CO—NR¹—CO—NHR²  (II)

in which R stands for a radical

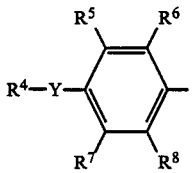

where $R^4$ stands for a phenyl which is optionally substituted by halogen, cyano, nitro, amino, alkyl, alkoxy, alkylthio, alkylsulphinyl, alkylsulphonyl, halogenoalkyl, halogenoalkoxy, halogenoallkylthio, halogenoalkylsulphonyl, hydroxycarbonyl, alkylcarbonyl, alkoxycarbonyl, aminocarbonyl, alkoxycarbonylamino and/or sulphonylamino or for the radical

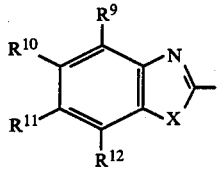

where $R^9$, $R^{10}$, $R^{11}$ and $R^{12}$ are identical or different and stand for hydrogen, halogen, alkyl, alkoxy, halogenoalkyl or halogenoalkoxy and X stands for oxygen, sulphur or a grouping —N═CH—, $R^5$, $R^6$, $R^7$ and $R^8$ are identical or different and stand for hydrogen, halogen, alkyl or alkoxy and Y stands for oxygen, sulphur or the groupings —CO—, —SO—, —SO₂—, —CH₂—, —CH₂O— or —OCH₂— and $R^1$ and $R^2$ stand for hydrogen, halogen and optionally substituted radicals from the group consisting of alkyl, alkoxy, alkylthio, alkylsulphonyl and aryl;

3. a process for preparing the new biurets of the formula (II), which is characterized in that isocyanates of the formula (IV)

R—NCO  (IV)

in which R has the meanings specified above in (2), are reacted with ureas of the formula (V)

R¹NH—CO—NHR²  (V)

in which $R^1$ and $R^2$ have the meanings specified above in (1), if desired in the presence of diluents;

4. a process for preparing the new biurets of the formula (II) in which $R^2$ stands for hydrogen, which is characterized in that in the 1st stage amines of the formula (VI)

R—NH₂  (VI)

is which R has the meanings specified above in (2), are reacted with compounds of the formula (VII)

R¹NCO  (VII)

in which $R^1$ has the meanings specified above in (1), at temperatures between 0° C. and 80° C. in the presence of inert diluents to give compounds of the formula (VIII)

R—NH—CO—NR¹H  (VIII)

in which R and $R^1$ have the meanings specified above in (2), and subsequently, if desired after their isolation, are reacted at temperatures between 0° C. and 80° C. in a 2nd stage with phosgene, if desired in the presence of inert diluents, to give the N-chlorocarbonylureas of the formula (IX)

R—NH—CO—NR¹—COCl  (IX)

in which R and $R^1$ have the meanings specified above in (2), and subsequently, if desired after their isolation, are reacted at temperatures between 0° C. and 100° C. in a 3rd stage with ammonia, if desired in the presence of inert diluents; and 5. new N-chlorocarbonylureas of the formula (IX)

R—NH—CO—NR¹—COCl  (IX)

in which R and $R^1$ have the meanings specified above in (2).

It is surprising that process (1) according to the invention can be used to prepare the compounds of the formula (I) in high purity and in high yields.

The advantage with this process is that the intermediates to be used can be prepared comparatively simply even on a large scale. Furthermore, the storage of the intermediates requires no expensive safety precautions.

Process (1) according to the invention is preferably used to prepare those compounds of the formula (I) in which R stands for optionally mono- or poly-substituted aryl having 6 to 10 carbon atoms, $R^1$ and $R^2$ stand for hydrogen, halogen, optionally halogen-substituted $C_1$–$C_6$-alkyl, $C_1$–$C_6$-alkoxy, $C_1$–$C_6$-alkylthio and $C_1$–$C_6$-alkylsulphonyl and for optionally halogen-, $C_1$–$C_2$-alkyl-, $C_1$–$C_2$-alkoxy-, $C_1$–$C_2$-alkylthio-, halogeno-$C_1$–$C_2$-alkyl-, halogeno-$C_1$–$C_2$-alkoxy- and/or halogeno-$C_1$–$C_2$-alkylthio-substituted aryl having 6 to 10 carbon atoms, but $R^1$ and $R^2$ must not both stand for hydrogen at the same time.

Particular preference is given to preparing those compounds of the formula (I) in which R has the meanings specified above in (2), $R^1$ and $R^2$ stand for hydrogen, fluorine, chlorine, bromine or for optionally fluorine-, chlorine- and/or bromine-substituted $C_1$–$C_4$-alkyl, $C_1$–$C_4$-alkoxy, $C_1$–$C_4$-alkylthio and $C_1$–$C_4$-alkylsulphonyl and for optionally fluorine-, chlorine-, bromine-, methyl-, methoxy-, methylthio-, trifluoromethyl-, trifluoromethoxy- and/or trifluoromethylthio- substituted phenyl, but $R^1$ and $R^2$ must not both stand for hydrogen at the same time.

Specific examples are the following compounds of the formula I:

1-[4-(4-Phenoxy)-phenyl]-, 1,[3,5-dichloro-4-(4-cyano-phenoxy)-phenyl]-, 1-[3,5-dichloro-4-(4-trifluoromethyl-sulphonyl-phenoxy)-phenyl-, 1-[3,5-dimethyl-4-(4-trifluoromethylsulphonyl-phenoxy)-phenyl]-, 1-[3-chloro-4-(4-trifluoromethylthio-phenoxy)-phenyl]-, 1-[3-methoxy-4-(4-trifluoromethylthio-phenoxy)-phenyl]-, 1-[2-chloro-4-(4-trifluoromethylthio-phenoxy)-phenyl]- and 1-[3-methyl-4-(5,6-dichloro-2-benzothiazolyloxy)-phenyl]-3-methyl-1,3,5,triazine-2,4,6-trione.

If for example process (1) according to the invention is carried out using diethyl carbonate and 1-methyl-5-[3-methyl-4-(4-trifluoromethylthiophenoxy)-phenyl]-biuret as starting materials and potassium tert.-butylate as an acid acceptor or 3-methyl-5-[3-methyl-4-(4-trifluoromethylthiophenoxy)-phenyl]-biuret and diethyl carbonate as starting materials and sodium methylate as an acid acceptor, then the reaction can be represented by the following formula diagrams:

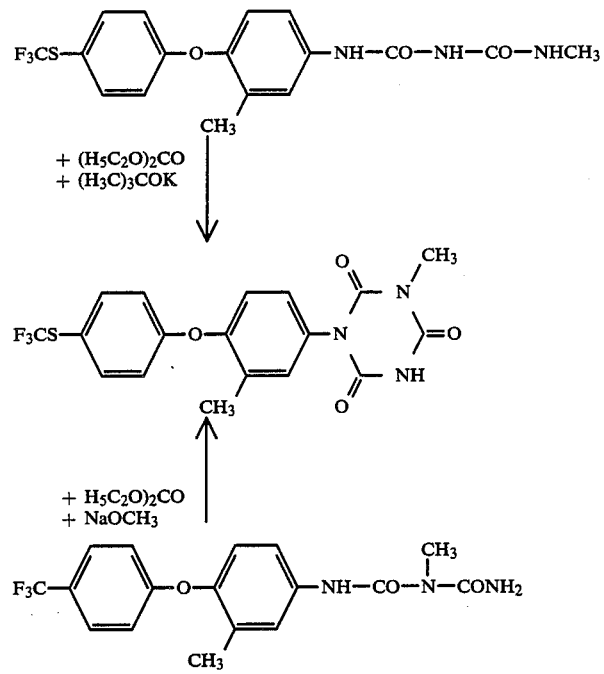

The compounds to be used as starting materials for process (1) according to the invention are defined in general by the formula (II). The compounds of the formula (II) are partly known (compare for example "Methoden der organischen Chemie" [Methods of organic chemistry], volume E IV, page 1040, (Houben-Weyl-Müller) Thieme Verlag Stuttgart). Preference is given to the use of compounds of the formula II in which R, $R^1$ and $R^2$ have the preferred meanings specified in the case of the compounds of the formula I. Specific examples which may be mentioned are: 1-methyl-5-[4-(-phenoxy)-phenyl]-, -5-[3,5-dichloro-4-(4-cyano-phenoxy)-phenyl]-, -5-[3,5-dichloro-4-(4-trifluoromethylsulphonyl-phenoxy)-phenyl-, -5-[3,5-dimethyl-4-(4-trifluoromethyl-sulphonyl-phenoxy)-phenyl]-, -5-[3-chloro-4-(4-trifluoromethylthio-phenoxy)-phenyl]-, -5-[3-methoxy-4-(4-trifluoromethylthio-phenoxy)-phenyl]-, -5-[2-chloro-4-(4-trifluoromethylthio-phenoxy)-phenyl]- and -5-[3-methyl-4-(5,6-dichloro-2-benzothiazolyloxy)-phenyl]-biuret and the corrresponding 3-methyl derivatives of these compounds.

Compounds of the formula (II) in which R, $R^1$ and $R^2$ have the meanings specified in (2) are new.

Preference is given to the new compounds of the formula (II) in which R stands for a radical

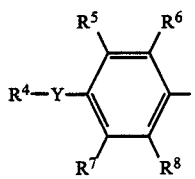

where R⁴ stands for a phenyl which is optionally substituted by halogen, such as fluorine, chlorine or or bromine, cyano, nitro, amino, $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, halogeno-$C_1$-alkyl, halogeno-$C_1$–$C_4$-alkoxy, halogeno-$C_1$–$C_4$-alkylthio, halogeno-$C_1$–$C_4$-alkyl-sulphonyl, hydroxycarbonyl, $C_1$–$C_4$-alkylcarbonyl, $C_1$–$C_4$-alkoxycarbonyl, aminocarbonyl, $C_1$–$C_4$-alkoxycarbonylamino and/or sulphonylamino or for the radical

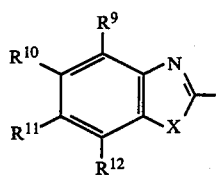

where $R^9$, $R^{10}$, $R^{11}$ and $R^{12}$ are identical or different and stand for hydrogen, halogen such as fluorine, chlorine or bromine, $C_1$–$C_4$-alkyl, $C_1$–$C_4$-alkoxy, halogeno-$C_1$–$C_4$-alkyl or halogeno-$C_1$–$C_4$-alkoxy and X stands for oxygen, sulphur or a grouping —N=CH—, $R^5$, $R^6$, $R^7$ and $R^8$ are identical or different and stand for hydrogen, halogen, such as fluorine, chlorine or bromine, $C_1$–$C_4$-alkyl or $C_1$–$C_4$-alkoxy and Y stands for oxygen, sulphur or the groupings —CO—, —SO—, $SO_2$—, —$CH_2$—, —$CH_2O$—, or —$OCH_2$— and $R^1$ and $R^2$ stand for hydrogen, halogen, for optionally halogen-substituted $C_1$–$C_6$-alkyl, $C_1$–$C_6$-alkoxy, $C_1$–$C_6$-alkylthio and $C_1$–$C_6$-alkylsulphonyl, and for optionally halogen-, $C_1$–$C_2$-alkyl-, $C_1$–$C_2$-alkoxy-, $C_1$–$C_2$-alkylthio-, halogeno-$C_1$–$C_2$-alkyl-, halogeno-$C_1$–$C_2$-alkoxy- and/or halogeno-$C_1$–$C_2$-alkylthio-substituted phenyl.

Particular preference is given to the new compounds of the formula (II) in which R stands for a radical

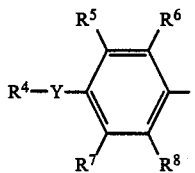

where R⁴ stands for a phenyl which is optionally substituted by fluorine, chlorine, bromine, cyano, nitro, amino, $C_1$–$C_2$-alkyl, $C_1$–$C_2$-alkoxy, $C_1$–$C_2$-alkylthio, $C_1$–$C_2$-alkylsulphinyl, $C_1$–$C_2$-alkylsulphonyl, halogeno-$C_1$–$C_4$-alkyl, halogeno-$C_1$–$C_2$-alkoxy, halogeno-$C_1$–$C_2$-alkylthio, halogeno-$C_1$–$C_2$-alkysulphonyl, $C_1$–$C_2$-alkylcarbonyl, $C_1$–$C_2$-alkoxycarbonyl, aminocarbonyl, $C_1$–$C_2$-alkoxycarbonylamino and/or sulphonylamino or for the radical

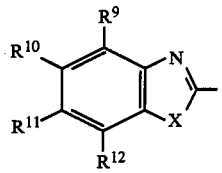

where $R^9$, $R^{10}$, $R^{11}$ and $R^{12}$ are identical or different and stand for hydrogen, fluorine, chlorine, bromine, $C_1$–$C_2$-alkyl, $C_1$–$C_2$-alkoxy, halogeno-$C_1$–$C_2$-alkyl or halogeno-$C_1$–$C_2$-alkoxy and X stands for oxygen, sulphur or a grouping —N=CH—, $R^5$, $R^6$, $R^7$ and $R^8$ are identical or different and stand for hydrogen, fluorine, chlorine, bromine, $C_1$–$C_2$-alkyl or $C_1$–$C_2$-alkoxy and Y stands for oxygen or sulphur and $R_1$ and $R_2$ stand for hydrogen, fluorine, chlorine, bromine or for optionally fluorine-, chlorine-, and/or bromine-substituted $C_1$–$C_4$-alkyl, $C_1$–$C_4$-alkoxy, $C_1$–$C_4$-alkylthio and $C_1$–$C_4$-alkylsulphonyl and for optionally fluorine-, chlorine-, bromine-, methyl-, methoxy-, methylthio-, trifluoromethyl-, trifluoromethoxy- and/or trifluoromethylthio-substituted phenyl.

Very particular preference is given to the new compounds of the formula (II) in which R stands for a radical

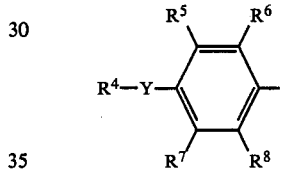

where R⁴ is a phenyl which is optionally substituted by fluorine, chlorine, bromine, cyano, nitro, trifluoromethyl, trifluoromethoxy, trifluoromethylthio, trifluoroethylthio and/or trifluoromethylsulphonyl or for the radical

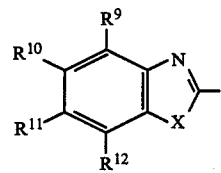

where $R^9$, $R^{10}$, $R^{11}$ and $R^{12}$ are identical or different and stand for hydrogen, fluorine, chlorine, bromine, methyl, methoxy, trifluoromethyl, dichlorofluoromethyl, chlorodifluoromethyl, trichloromethyl or trifluoromethoxy and X stands for oxygen, sulphur or a grouping —N=CH—, $R^5$, $R^6$, $R^7$ and $R^8$ are identical or different and stand for hydrogen, chlorine, methyl or methoxy and Y stands for oxygen or sulphur and $R^1$ and $R^2$ stand for hydrogen, fluorine, chlorine, bromine or for optionally fluorine, chlorine- and/or bromine-substituted methyl, ethyl, methoxy, ethoxy, methylthio, ethylthio, methylsulphonyl and ethylsulphonyl and for optionally fluorine-, chlorine-, bromine-, methyl-, methoxy-, methylthio-, trifluoromethyl-, trifluoromethoxy- and/or trifluoromethylthio-substituted phenyl, but $R^1$ and $R^2$ do not both stand for hydrogen at the same time.

Specific examples are the following new compounds of the formula II:

1-Methyl-5-[4-(4-phenoxy)-phenyl]-5-[3,5-dichloro-4-(4-phenoxy)-phenyl]-, -5-[3,5-dichloro-4-(4-trifluoromethyl-sulphonyl-phenoxy)-phenyl]-, -5-[3,5-dimethyl-4-(4-trifluoromethyl-sulphonyl-phenoxy)-phenyl]-, -5-[3-chloro-4-(4-trifluoromethylthio-phenoxy)-phenyl]-, -5-[3-methoxy)-4-(4-trifluoromethylthio-phenoxy)-phenyl]-, -5-[2-chloro-4-(4-trifluoromethylthio-phenoxy)-phenyl]- and -5-[3-methyl-4-(5,6-dichloro-2-benzothiazolyloxy)-phenyl]-biuret and the corresponding 3-methyl derivatives of these compounds.

The new compounds of the formula (II) can be prepared (see hereinafter) in accordance with process 3 according to the invention (above).

The dialkyl carbonates also to be used as starting materials for process (1) according to the invention are defined in general terms by the formula (III).

In this formula, $R^3$ stands for alkyl. Preferably $R^3$ stands for $C_1$-$C_4$-alkyl.

The compounds of the formula (III) are known compounds of organic chemistry.

Exammples of compounds of the formula (III) are: dimethyl carbonate, diethyl carbonate and di-n-propyl carbonate.

Process (1) according to the invention for preparing the compounds of the formula (I) is preferably carried out without diluent. The process is preferably carried out in the presence of excess dialkyl carbonate of the formula (III).

Process (1) according to the invention is carried out in the presence of strong bases. Particularly suitable are alkali metal alcoholates, such as sodium and potassium methylate or ethylate and potassium tert.-butylate.

Process (1) according to the invention is generally carried out at temperatures between 0° C. and 140° C. Preference is given to the range between 20° C. and 120° C. The reactions are generally carried out under normal pressure.

To carry out process (1) according to the invention, the amounts used per mol of the compound of the formula (II) are 1 to 3 mols, preferably 1 to 2 mols, of a strong base and from 5 to 30 mols, preferably 10 to 25 mols, of dialkyl carbonate of the formula (III). Working up is effected in conventional manner, for example by addition of water to the reaction mixture and neutralization with for example hydrochloric acid. If desired, the mixture then has added to it an organic solvent, such as, for example, methylene chloride, and the organic phase is worked up in conventional manner by washing, drying and removal of the solvent by distillation.

If for example process (3) according to the invention is carried out using 3-methyl-4-(4-trifluoromethylthio-phenoxy)-phenyl isocyanate and 1-methylurea as starting materials, then the reaction can be represented by the following formula diagram:

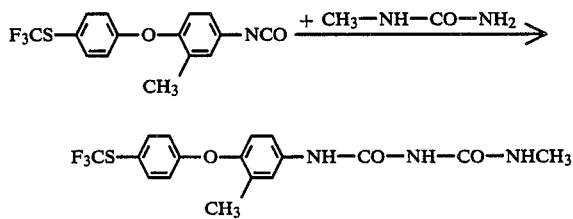

The compounds to be used as starting materials for process (3) according to the invention are defined in general terms by the formula (IV). In this formula, R preferably stands for those radicals which are specified as preferred for compounds of the formula (II). Specific examples are the following compounds of the formula IV:

4-(4-Phenoxy)-phenyl, 3,5-dichloro-4-(4-cyanophenoxy)-phenyl, 3,5-dichloro-4-(4-trifluoromethylsulphonyl)-phenoxy)-phenyl, 3,5-dimethyl-4-(4-trifluoromethyl-sulphonyl-phenoxy)-phenyl, 3-chloro-4-(4-trifluoromethylthio-phenoxy)-phenyl, 3-methoxy-4-(4-trifluoromethylthio-phenoxy)-phenyl, 2-chloro-4-(4-trifluoromethylthio-phenoxy)-phenyl and 3-methyl-4-(5,6-dichloro-2-benzothiazolyloxy)-phenyl isocyanate.

The compounds of the formula (IV) are known or can be prepared by known methods (cf. for example EP-OS (European Published Specification) 93,976).

The compounds additionally to be used as starting materials for the process according to the invention are defined in general terms by the formula (V). In this formula, $R^1$ and $R^2$ preferably stand for those radicals which are specified above as preferred for compounds of the formula (II).

If use is made of ureas of the formula (V) in which $R^1$ and $R^2$ stand for hydrogen, preference is given to preparing the biurets of the formula (II) in which $R^1$ stands for hydrogen. The isomeric biurets of the formula (II) in which $R^2$ stands for hydrogen are formed in the preparation as by-products. The ratio of these two isomers of the formula (II) can be varied by varying the reaction conditions.

The compounds of the formula (V) are known compounds of organic chemistry.

Process (3) according to the invention for preparing the compounds of the formula (II) is preferably carried out using diluents. The diluents can be practically any inert organic solvents.

These include in particular aliphatic and aromatic, optionally halogenated, hydrocarbons, such as pentane, hexane, heptane, cyclohexane, petroleum ether, naphtha, ligroin, benzene, toluene, xylene, methylene chloride, ethylene chloride, chloroform, carbon tetrachloride, chlorobenzene, o-dichlorobenzene, ethers such as diethyl and dibutyl ether, glycol dimethyl ether and diglycol dimethyl ether, tetrahydrofuran and dioxane, ketones, such as acetone, methyl ethyl, methyl isopropyl and methyl isobutyl ketone, esters, such as methyl acetate, ethyl acetate and diethyl carbonate, nitriles, such as, for example, acetonitrile and propionitrile, amides, such as, for example, dimethylformamide, dimethylacetamide and N-methylpyrrolidone, and also dimethyl sulphoxide, tetramethylene sulphone, hexamethylphosphoramide and pyridine.

The reaction temperatures at which process (3) according to the invention is carried out can be varied within a relatively wide range. In general, the process is carried out at temperatures between 0° C. and 140° C., preferably between 0° C. and 120° C. The reactions are generally carried out under normal pressure.

In carrying out process (3), the amount used per mol of the compound of the formula (IV) is 1 to 2 mols, preferably 1.0 to 1.4 mols, of urea of the formula (V). The reaction product is worked up in conventional manner.

If for example process (4) according to the invention is carried out using as starting materials 3-methyl-4-(4-trifluoromethylthiophenoxy)-aniline, methyl isocyanate, phosgene and ammonia, then the reaction can be represented by the following reaction diagram:

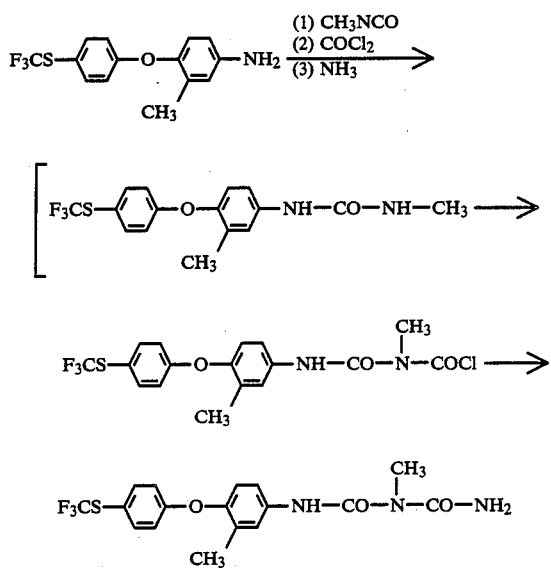

The amines to be used as starting materials for the 1st stage of process (4) according to the invention are defined in general terms by the formula (VI). In this formula, R preferably stands for those radicals which are specified above as preferred for compounds of the formula (II).

Specific examples are the following compounds of the formula VI:

4-Phenoxy-, 3,5-dichloro-4-(4-cyanophenoxy)-, 3,5-dichloro-4-(4-trifluoromethylsulphonylphenoxy)-, 3,5-dimethyl-4-(4-trifluoromethylsulphonylphenoxy)-, 3-chloro-4-(4-trifluoromethylthiophenoxy)-, 3-methoxy-4-(4-trifluoromethylthiophenoxy)-, 2-chloro-4-(4-trifluoromethylthiophenoxy)- and 3-methyl-4-(5,6-dichloro-2-benzothiazolyloxy)-aniline.

The compounds of the formula (VI) are known or can be prepared by known methods (cf. for example DE-OS (German Published Specification) 2,413,722 and DE-OS (German Published Specification) 2,718,799).

The compound of the formula (VIa) 3-methyl-4-(4-trifluoromethylthiophenoxy)-aniline is new:

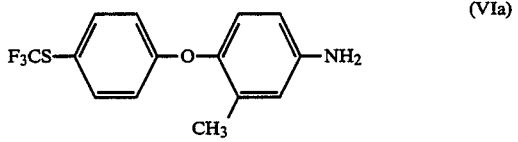

(VIa)

This compound is prepared by hydrogenating 3-methyl-4-(4-trifluoromethylthiophenoxy)-nitrobenzene with hydrogen at temperatures between 20° C. and 150° C. and under a pressure between 5 and 150 bar in the presence of hydrogenation catalysts, such as, for example, Raney nickel, in the presence of diluents such as, for example, toluene.

3-Methyl-4-(4-trifluoromethylthiophenoxy)-nitrobenzene is likewise new and can for example be prepared by reacting 4-trifluoromethylthiophenol with 2-methyl-4-nitrochlorobenzene in the presence of acid acceptors, such as, for example, sodium hydroxide, and in the presence of diluents, such as, for example, dimethyl sulphoxide, at temperatures between 0° C. and 200° C.

4-Trifluoromethylthiophenol and 2-methyl-4-nitrochlorobenzene are commonly known compounds of organic chemistry.

The compounds further to be used as starting materials for the 1st stage of process (4) according to the invention are defined in general terms by the formula (VII).

In this formula, $R^1$ preferably stands for those radicals which are specified above as preferred for compounds of the formula (II). Specific examples are the following compounds of the formula VII:

Methyl isocyanate, ethyl isocyanate, n-propyl isocyanate, phenyl isocyanate, 4-chlorophenyl isocyanate.

The compounds of the formula (VII) are commonly known compounds of organic chemistry.

The compounds to be used as starting materials for the 2nd stage of process (4) according to the invention are defined in general terms by the formula (VIII). In this formula, R and $R^1$ preferably stand for those radicals which are specified above as preferred for compounds of the formula (II).

Specific examples are the following compounds of the formula VIII:

1-Methyl-3-[4-(4-phenoxy)-phenyl]-,-3-[3,5-dichloro-4-(4-cyanophenoxy)-phenyl]-,-3-[3,5-dichloro-4-(4-trifluoromethylsulphonylphenoxy)-phenyl]-,-3-[3,5-dimethyl-4-(4-trifluoromethylsulphonylphenoxy)-phenyl]-, 3-[3-chloro-4-(4-trifluoromethylthiophenoxy]-phenyl]-,-3-[3-methoxy-4-(4-trifluoromethylthiophenoxy)-phenyl]-,-3-[2-chloro-4-(4-trifluoromethylthiophenoxy)-phenyl]- and -3-[3-methyl-4-(5,6-dichloro-2-benzothiazolyloxy)-phenyl]-urea.

The compounds of the formula (VIII) are known or can be prepared by known methods (cf. for example DE-OS (German Published Specification) 2,413,722 and DE-OS (German Published Specification) 2,718,799).

The compounds to be used as starting materials for the 3rd stage of process (4) according to the invention are defined in general terms by the formula (IX). In this formula, R and $R^1$ preferably stand for those radicals which are specified above as preferred for compounds of the formula (II).

The compounds of the formula (IX) are partly known (cf. for example "Methoden der organischen Chemie" [Methods of Organic Chemistry], Volume E IV, page 1026 Houben-Weyl-Müller, Verlag Stuttgart).

N-Chlorocarbonylureas of the formula (IX) in which R stands for a radical

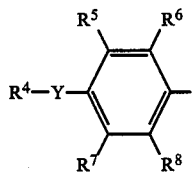

where $R^4$ stands for a phenyl which is optionally substituted by halogen, cyano, nitro, amino, alkyl, alkoxy, alkylthio, alkylsulphinyl, alkylsulphonyl, halogenoalkyl, halogenoalkoxy, halogenoalkylthio, halogenoalkylsulphonyl, hydroxycarbonyl, alkylcarbonyl, alkoxycarbonyl, aminocarbonyl, alkoxycarbonylamino and/or sulphonylamino or for the radical

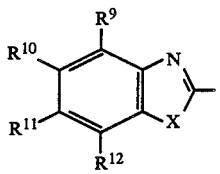

where $R^{10}$, $R^{11}$ and $R^{12}$ are identical or different and stand for hydrogen, halogen, alkyl, alkoxy, halogenoalkyl or halogenoalkoxy and X stands for oxygen, sulphur or the groupings —N=CH—, $R^5$, $R^6$, $R^7$ and $R^8$ are identical or different and stand for hydrogen, halogen, alkyl or alkoxy and Y stands for oxygen, sulphur or the groupings —CO—, —SO—, $SO_2$—, —$CH_2$—, —$CH_2O$— or —$OCH_2$— and $R^1$ stands for hydrogen, halogen and optionally substituted radicals from the group consisting of alkyl, alkoxy, alkylthio, alkylsulphonyl and aryl are new.

Preference is given to the new compounds of the formula (IX) in which R stands for a radical

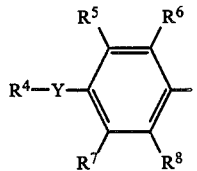

where $R^4$ stands for a phenyl which is optionally substituted by halogen, such as fluorine, chlorine, or bromine, cyano, nitro, amino, $C_1$-$C_4$-alkyl, $C_1$-$C_4$-alkoxy, $C_1$-$C_4$-alkylthio, $C_1$-$C_4$-alkyl-sulphinyl, $C_1$-$C_4$-alkyl-sulphonyl, halogeno-$C_1$-$C_4$-alkyl, halogeno-$C_1$-$C_4$-alkoxy, halogeno-$C_1$-$C_4$-alkyl-thio, halogen-$C_1$-$C_4$-alkylsulphonyl, hydroxy-carbonyl, $C_1$-$C_4$-alkylcarbonyl, $C_1$-$C_4$-alkoxy-carbonyl, aminocarbonyl, $C_1$-$C_4$-alkoxycarbonyl-amino and/or sulphonylamino or for the radical

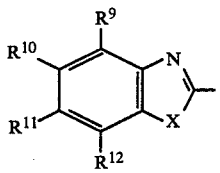

where $R^9$, $R^{10}$, $R^{11}$ and $R^{12}$ are identical or different and stand for hydrogen, halogen, such as fluorine, chlorine or bromine, $C_1$-$C_4$-alkyl, $C_1$-$C_4$-alkoxy, halogeno-$C_1$-$C_4$-alkyl or halogeno-$C_1$-$C_4$-alkoxy and X stands for oxygen, sulphur or a groupings —N=CH—, $R^5$, $R^6$, $R^7$ and $R^8$ are identical or different and stand for hydrogen, fluorine, chlorine, bromine, $C_1$-$C_4$-alkyl or $C_1$-$C_4$-alkoxy and Y stands for oxygen, sulphur or the groupings —CO—, —SO—, $SO_2$—, —$CH_2$—, —$CH_2O$— or —$OCH_2$— and $R^1$ stands for hydrogen, halogen, for optionally halogen-substituted $C_1$-$C_6$-alkyl, $C_1$-$C_6$-alkoxy, $C_1$-$C_6$-alkylthio and $C_1$-$C_6$-alkylsulphonyl and for optionally halogen-, $C_1$-$C_2$-alkyl-, $C_1$-$C_2$-alkoxy-, $C_1$-$C_2$-alkylthio-, halogeno-$C_1$-$C_2$-alkyl-, halogeno-$C_1$-$C_2$-alkoxy- and/or halogeno-$C_1$-$C_2$-alkylthio-substituted phenyl.

Particular preference is given to the new compounds of the formula (IX) in which R stands for a radical

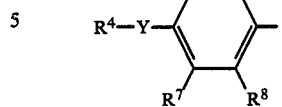

where $R^4$ stands for a phenyl which is optionally substituted by fluorine, chlorine, bromine, cyano, nitro, amino, $C_1$-$C_2$-alkyl, $C_1$-$C_2$-alkoxy, $C_1$-$C_2$-alkylthio, $C_1$-$C_2$-alkylsulphinyl, $C_1$-$C_2$-alkylsulphonyl, halogeno-$C_1$-$C_2$-alkyl, halogeno-$C_1$-$C_2$-alkoxy, halogeno-$C_1$-$C_2$-alkylthio, halogeno-$C_1$-$C_2$-alkylsulphonyl, hydroxycarbonyl, $C_1$-$C_2$-alkylcarbonyl, $C_1$-$C_2$-alkoxycarbonyl, aminocarbonyl, $C_1$-$C_2$-alkoxycarbonylamino and/or sulphonylamino or for the radical

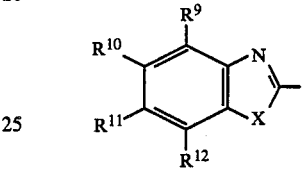

where $R^9$, $R^{10}$, $R^{11}$ and $R^{12}$ are identical or different and stand for hydrogen, fluorine, chlorine, bromine, $C_1$-$C_2$-alkyl, $C_1$-$C_2$-alkoxy, halogeno-$C_1$-$C_2$-alkyl or halogeno-$C_1$-$C_2$-alkoxy and X stands for oxygen, sulphur or a grouping —N=CH—, $R^5$, $R^6$, $R^7$ and $R^8$ are identical or different and stand for hydrogen, fluorine, chlorine, bromine, $C_1$-$C_2$-alkyl or $C_1$-$C_2$-alkoxy and Y stands for oxygen or sulphur and $R^1$ stands for hydrogen, fluorine, chlorine, bromine or for optionally fluorine-, chlorine- and/or bromine-substituted $C_1$-$C_4$-alkyl, $C_1$-$C_4$-alkoxy, $C_1$-$C_4$-alkylthio and $C_1$-$C_4$-alkylsulphonyl and for optionally fluorine-, chlorine-, methyl-, methoxy-, methylthio-, trifluoromethyl-, trifluoromethoxy- and/or trifluoromethylthio-substituted phenyl.

Very particular preference is given to the new compounds of the formula (IX) in which R stands for the radical

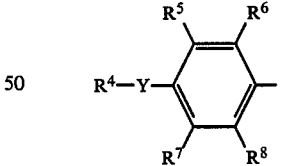

where $R^4$ stands for a phenyl which is optionally substituted by fluorine, chlorine, bromine, cyano, nitro, trifluoromethyl, trifluoromethoxy, trifluoromethylthio, trifluoroethylthio and/or trifluoromethylsulphonyl or for the radical

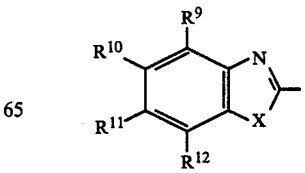

R⁹, R¹⁰, R¹¹ and R¹² are identical or different and stand for hydrogen, fluorine, chlorine, bromine, methyl, methoxy, trifluoromethyl, dichlorofluoromethyl, chlorodifluoromethyl, trichloromethyl or trifluoromethoxy and X stands for oxygen, sulphur or a grouping —N=C—, R⁵, R⁶, R⁷ and R⁸ are identical or different and stand for hydrogen, chlorine, methyl or methoxy and Y stands for oxygen or sulphur and R¹ stands for hydrogen, fluorine, chlorine, bromine or for optionally fluorine-, chlorine- and/or bromine-substituted methyl, ethyl, methoxy, ethoxy, methylthio, ethylthio, methylsulphonyl and ethylsulphonyl and for optionally fluorine-, chlorine-, bromine-, methyl-, methoxy-, methylthio-, trifluoromethyl-, trifluoromethoxy- and/or trifluoromethylthio-substituted phenyl.

Specific examples are the following compounds of the formula IX:

1-Chlorocarbonyl-1-methyl-3-[4-(4-phenoxy)-phenyl]-3-[3,5-dichloro-4-(4-cyanophenoxy)-phenyl]-, -3-[3,5-dichloro-4-(4-trifluoromethylsulphonylphenoxy)-phenyl-, -3-[3,5-dimethyl-4-(4-trifluoromethylsulphonylphenoxy)phenyl]-, -3-[3-chloro-4-(4-trifluoromethylthiophenoxy)phenyl]-, -3-[3-methoxy-4-(4-trifluoromethylthiophenoxy)phenyl]-, -3-[2-chloro-4-(4-trifluoromethylthiophenoxy)phenyl]- and -3-[3-methyl-4-(5,6-dichloro-2-benzothiazolyloxy)-phenyl]-urea.

The N-chlorocarbonylureas of the formula (IX) can be prepared as in stage 2 of process (4) according to the invention and are subsequently reacted as per stage 3 of process (4) according to the invention to give the compounds of the formula (II) in which R² stands for hydrogen.

Process (4) according to the invention is preferably carried out in all three stages using diluents. Possible diluents are the organic solvents already mentioned for process (3) according to the invention.

The reaction temperatures at which process (4) according to the invention is carried out can be varied within a relatively wide range in all three stages.

In general the process is carried out in all stages at temperatures between 0° C. and 100° C., preferably between 15° C. and 80° C. The reactions are generally carried out under normal pressure.

In carrying out process (4), the amounts used in the 1st stage per mol of amine of the formula (VI) are 1 to 2 mols, preferably 1 to 1.5 mols of the compound of the formula (VII), subsequently in the 2nd stage, if desired after isolation of the compound of the formula (VIII), 1.0 to 3.0 mols, preferably 1.5 to 2.5 mols, of phosgene are added and then in the 3rd stage, if desired after isolation of the N-chlorocarbonylureas of the formula (IX), ammonia is passed in until complete conversion of the compounds of the formula (IX). Working up is effected in conventional manner.

The individual stages of process (4) according to the invention can also be carried out separately in that, after each stage, the compounds formed are isolated and purified. They can then be reacted further or be used in some other way.

The compounds of the formula (I) which are producible by process (1) according to the invention have an excellent growth-promoting action on animals and an outstanding coccidiostatic action [cf. for example DE-OS (German Published Specification) 2,413,722 and U.S. Pat. No. 4,219,552].

PREPARATION EXAMPLES

Example 1

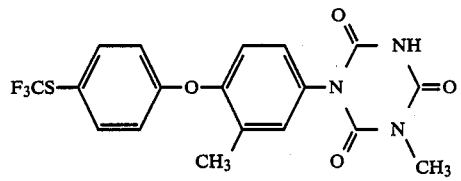

399 g (1 mol) of 1-methyl-5-[3-methyl-4-(4-trifluoromethylthiophenoxy)-phenyl]-biuret, 108 g (2 mol) of sodium methylate and 2,400 ml of diethyl carbonate are refluxed for 3 hours. The resulting alcohol is distilled off at the same time. The mixture is cooled down to 25° C., has 4,800 g of water added to it and is neutralized with hydrochloric acid, and the organic phase is separated off. The aqueous phase is extracted once with diethyl carbonate. The combined organic phases are concentrated in a water jet vacuum.

This gives 421 g (94% of theory) of 1-[3-methyl-4-(4-trifluoromethylthiophenoxy)-phenyl]-3-methyl-1,3,5-triazine-2,4,6-trione of 95% purity having a melting point of 191° C. (ethanol).

Example 2

2 g (0.005 mol) of 99.3% pure 3-methyl-5-[3-methyl-4-(4-trifluoromethylthiophenoxy)-phenyl]-biuret, 0.7 g (0.01 mol) of sodium methylate and 10 g of diethyl carbonate are stirred at 20° C. for 3 hours. This is followed by addition of water, neutralization with hydrochloric acid and extraction with methylene chloride. The organic phase is separated off, dried and concentrated.

Incipient distillation leaves 2.1 g (100% of theory) of 1-[3-methyl-4-(4-trifluoromethylthiophenoxy)-phenyl]-3-methyl-1,3,5-triazine-2,4,6-trione of 97.3% purity having a melting point of 190° C.

Starting materials of the formula (II)

Example 3

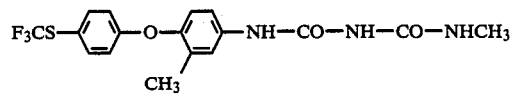

(Process 3)

325.3 g (1 mol) of 3-methyl-4-(4-trifluoromethylthiophenoxy)-phenyl isocyanate, 74.1 g (1 mol) of methylurea and 95 ml of methylene chloride are refluxed for 3 hours. 230 ml of methylene chloride are then added, and the mixture is cooled down to 0° C. The product is filtered off and dried.

This gives 298 g (75% of theory) of 1-methyl-5-[3-methyl-4-(4-trifluoromethylthiophenoxy)-phenyl]-biuret having a melting point of 153° C. (naphtha).

Example 4

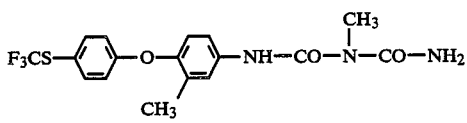

(Process (4) "single-vessel process")

To 4.2 g (0.014 mol) of 3-methyl-4-(4-trifluoromethylthiophenoxy)-aniline in 40 ml of toluene is added dropwise at 20° C., 0.84 g (0.015 mol) of methyl isocyanate, which is followed by about 12 hours of stirring. 12.5 g of 20% strength phosgene solution in toluene (0.025 mol) are then added dropwise, which is followed by 8 hours of stirring at 20° C. and subsequent heating at 60° C. for 3 hours. After a thin layer chromatography check for complete conversion, ammonia is passed at 20° C. through this solution until N-chlorocarbonylurea is no longer detectable by thin layer chromatography. The mixture is then filtered with suction, and the residue is thoroughly stirred with water, filtered off and dried.

This gives 5.2 g (93% of theory) of 3-methyl-5-[3-methyl-4-(4-trifluoromethylthiophenoxy)-phenyl]-biuret of 98.5% purity having a melting point of 182°–183° C.

Example 5

Ammonia is passed at below 20° C. through a solution of 4.2 g (0.01 mol) of 1-chlorocarbonyl-1-methyl-3-[3-methyl-4-(4-trifluoromethylthiophenoxy)-phenyl]urea (cf. Example 9) in 20 ml of toluene until all the starting material has disappeared. The mixture is then filtered with suction, and the residue is stirred with 40 ml of water, filtered off and dried.

This gives 3.8 g (95% of theory) of 3-methyl-5-[3-methyl-4-(4-trifluoromethylthiophenoxy)-phenyl]-biuret of 99% purity having a melting point of 182° C.

Starting compound of the formula (IV)

Example 6

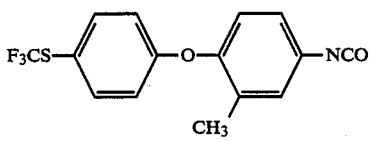

480 g of chlorobenzene and 180 g of phosgene are presented at 0° C., and a solution of 300 g (1 mol) of 3-methyl-4-(4-trifluoromethylthiophenoxy)-aniline in 550 g of chlorobenzene is added in the course of 30 minutes during which the temperature rises to 25° C. This is followed by heating to the boil in the course of 1 hour, in the course of which further phosgene is passed in from 80° C. until hydrogen chloride is no longer detectable (about 1 hour).

Excess phosgene is flushed out with nitrogen, the solvent is drawn off and the crude product is distilled.

This gives 316 g (96% of theory) of 3-methyl-4-(4-trifluoromethylthiophenoxy)-phenyl isocyanate of 99% purity having a boiling point of 162° C./2 mbar.

Starting compound of the formula (VI)

Example 7

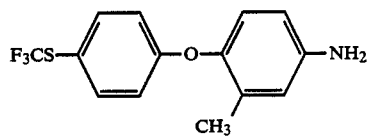

329.3 g (1 mol) of 3-methyl-4-(4-trifluoromethylthiophenoxy)-nitrobenzene are dissolved in 1,100 g of toluene and after addition of 20 g of Raney nickel are hydrogenated at 90° C. and a hydrogen pressure for 90 bar. When the absorption of hydrogen has ceased the catalyst is filtered off, the solvent is distilled off and the product is rectified in an oil pump vacuum.

This gives 270.7 g (90% of theory) of 3-methyl-4-(4-trifluoromethylthiophenoxy)-aniline having a purity of 99.5% and a melting point of 44°–45° C.

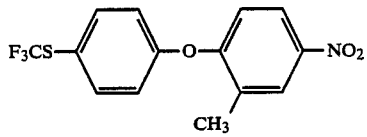

198.1 g (1.02 mols) of 4-trifluoromethylthiophenol are presented in 330 g of dimethyl sulphoxide. At 20° C. 44.0 g (1.1 mol) of sodium hydroxide chips are added and dissolved by heating to 90° C. 171.6 g (1 mol) of 2-methyl-4-nitrochlorobenzene dissolved in 330 g of dimethyl sulphoxide are added in the course of 30 minutes. The temperature is then raised from 90° C. to 140° C. and stirring is continued for 3 hours. The solvent is distilled off at 140° C. in the course of 2 hours during which the pressure is gradually reduced to 10 to 20 mbar. The residue is then cooled down to 20° C., and 1 lit of water is added. The resulting suspension is filtered, the precipitate is washed with dilute sodium hydroxide solution and water, is dried and recrystallized from petroleum ether.

This gives 281.3 g (85% of theory) of 3-methyl-4-(4-trifluoromethylthiophenoxy)-nitrobenzene having a purity of 99.5% and a melting point of 61°–62° C.

Starting compound of the formula (VIII)

Example 8

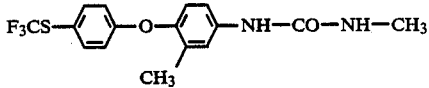

748.3 g (2.5 mols) of 3-methyl-4-(4-trifluoromethylthiophenoxy)-aniline are dissolved in 2,170 g of anhydrous toluene, 157 g (2.75 mols) of methyl isocyanate are added at 40° C. in the course of 2 hours, and the mixture is then stirred for a further 3 hours. Excess methyl isocyanate is distilled off with 600 g of toluene in vacuo. The residue is then stirred at 10° C. for a further hour. The product is filtered off, is washed with toluene at 10° C. and is dried.

This gives 881.9 g (98% of theory) of 1-methyl-3-[3-methyl-4-(4-trifluoromethylthiophenoxy)-phenyl]-urea having a purity of 99% and a melting point of 129°–130° C.

Starting compound of the formula (IX)

Example 9

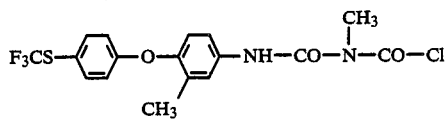

7.1 g (0.02 mol) of 1-methyl-3-[3-methyl-4-(4-trifluoromethylthiophenoxy)-phenyl]-urea in 25 ml of toluene have added to them dropwise at 20° C. 17.8 g of a 20% strength solution (0.036 mol) of phosgene in toluene, are stirred at 20° C. for a further 15 to 16 hours and are then heated at 50° C. to 60° C. for a further 4 hours.

Concentration and incipient distillation leave 8.4 g (100% of theory) of 1-chlorocarbonyl-1-methyl-3-[3-methyl-4-(4-trifluoromethylthiophenoxy)-phenyl]-urea having a purity of 94% and a melting point of 79° C.

It will be understood that the specification and examples are illustrative but not limitative of the present invention and that other embodiments within the spirit and scope of the invention will suggest themselves to those skilled in the art.

What is claimed is:

1. A process for preparing a 1,3,5-triazinetrione of the formula

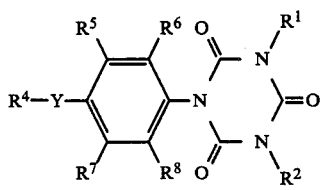

in which $R^4$ stands for a phenyl which is optionally substituted by halogen, cyano, nitro, amino, alkyl, alkoxy, alkylthio, alkylsulphinyl, alkylsulphonyl, halogenoalkyl, halogenoalkoxy, halogenoalkylthio, halogenoalkylsulphonyl, hydroxycarbonyl, alkylcarbonyl, alkoxycarbonyl, aminocarbonyl, alkoxycarbonylamino and/or sulphonylamino or for the radical

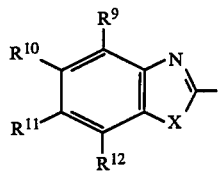

where $R^9$, $R^{10}$, $R^{11}$ and $R^{12}$ are identical or different and stand for hydrogen, halogen, alkyl, alkoxy, halogenoalkyl or halogenoalkoxy, X stands for oxygen, sulphur or a grouping —N=CH—, $R^5$, $R^6$, $R^7$ and $R^8$ are identical or different and stand for hydrogen, halogen, alkyl or alkoxy, Y stands for oxygen, sulphur or the groupings —CO—, —SO—, —SO$_2$—, —CH$_2$—, —CH$_2$O— or —OCH$_2$—, and $R^1$ and $R^2$ stand for hydrogen, halogen and optionally halogen-substituted $C_1$-$C_6$-alkyl, $C_1$-$C_6$-alkoxy, $C_1$-$C_6$-alkylthio and $C_1$-$C_6$-alkylsulphonyl and for optionally halogeno-, $C_1$-$C_2$-alkyl-, $C_1$-$C_2$-alkoxy-, $C_1$-$C_2$-alkylthio-, halogeno-$C_1$-$C_2$-alkyl-, halogeno-$C_1$-$C_2$-alkoxy- and/or halogeno-$C_1$-$C_2$-alkylthio-substituted aryl having 6 to 10 carbon atoms, comprising reacting a biuret of the formula $$R-NH-CO-NR^1-CO-NHR^2 \qquad (II)$$

in which R is

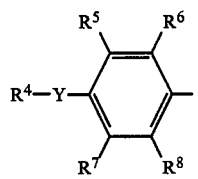

with a dialkyl carbonate of the formula $$(R^3O)_2CO \qquad (III)$$

in which $R^3$ stands for alkyl, in the presence of sodium methylate and distilling off by-product alcohol.

2. The process according to claim 1, wherein the 1,3,5-triazinetrione which is produced is 1-[3-methyl-4-(4-trifluoromethylthiophenoxy)-phenyl]-3-methyl-1,3,5-triazine-2,4,6-trione

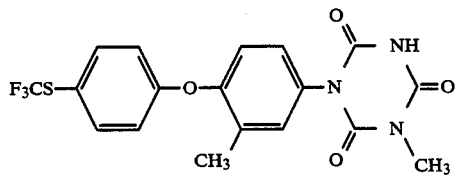

* * * * *